US00PP33584P2

(12) United States Plant Patent
Heuger

(10) Patent No.: US PP33,584 P2
(45) Date of Patent: Oct. 26, 2021

(54) ***HELLEBORUS* PLANT NAMED 'COSEH 6400'**

(50) Latin Name: ***Helleborus* x *ballardiae* X *Helleborus* x *hybridus***
Varietal Denomination: COSEH 6400

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 140 days.

(21) Appl. No.: 16/873,645

(22) Filed: May 27, 2020

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
CPC ..... A01H 5/02; A01H 5/00; A01H 6/72
See application file for complete search history.

*Primary Examiner* — June Hwu
(74) *Attorney, Agent, or Firm* — C. Anne Whealy

(57) ABSTRACT

A new and distinct cultivar of *Helleborus* plant named 'COSEH 6400', characterized by its upright to slightly outwardly spreading and mounded plant habit; vigorous growth habit; dark green-colored leaves; freely flowering habit; light yellow green-colored flowers with greyed purple-colored margins; and good garden performance.

2 Drawing Sheets

Figure 1:
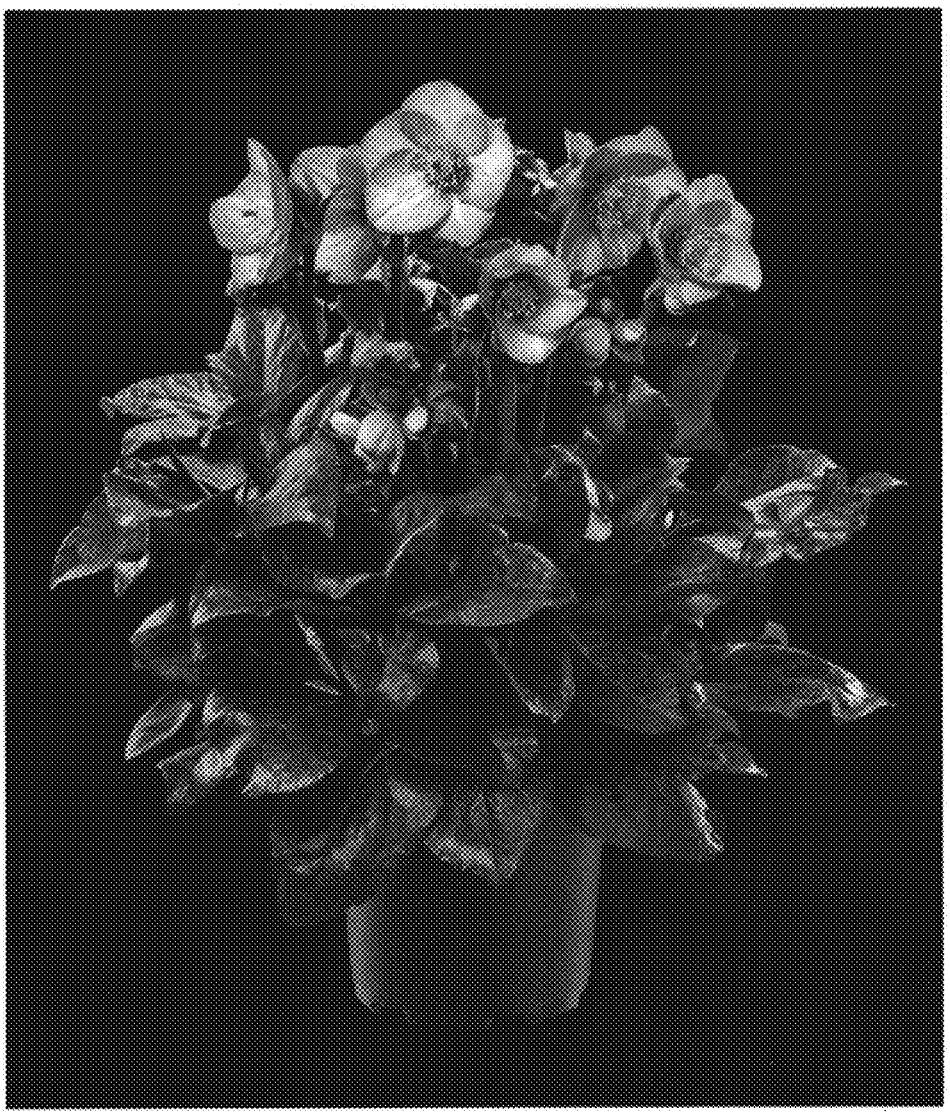

Botanical designation: *Helleborus* x *ballardiae* X *Helleborus* x *hybridus*.
Cultivar denomination: 'COSEH 6400'.

CROSS-REFERENCED TO CLOSELY-RELATED APPLICATIONS

Title: *Helleborus* Plant Named 'COSEH 6500'
Inventor/Applicant: Josef Heuger
Filed: Concurrently with the instant application U.S. Plant patent application Ser. No. 16/873,638)
Title: *Helleborus* Plant Named 'COSEH 6600'
Inventor/Applicant: Josef Heuger
Filed: Concurrently with the instant application U.S. Plant patent application Ser. No. 16/873,637)

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Jun. 6, 2019, application number 2019/1387. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus* x *ballardiae* X *Helleborus* x *hybridus* and hereinafter referred to by the name 'COSEH 6400'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in December, 2012 of a proprietary selection of *Helleborus* x *ballardiae* identified as code number P839, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in January, 2015.

Asexual reproduction of the new *Helleborus* plant by in vitro axillary meristem culture in a controlled environment in Glandorf, Germany since March, 2015 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 6400'. These characteristics in combination distinguish 'COSEH 6400' as a new and distinct *Helleborus* plant:

1. Upright to slightly outwardly spreading and mounded plant habit.
2. Vigorous growth habit.
3. Dark green-colored leaves.

4. Freely flowering habit.
5. Light yellow green-colored flowers with greyed purple-colored margins.
6. Good garden performance.

Plants of the new *Helleborus* differ from plants of the female parent selection in the following characteristics:

1. Plants of the new *Helleborus* are more vigorous than plants of the female parent selection.
2. Plants of the new *Helleborus* flower later than plants of the female parent selection.

Plants of the new *Helleborus* differ from plants of the male parent selection in the following characteristics:

1. Plants of the new *Helleborus* are more vigorous than plants of the male parent selection.
2. Flowers of plants of the new *Helleborus* are light yellow green in color with greyed purple-colored margins whereas flowers of plants of the male parent selection are cream and brown in color.

Plants of the new *Helleborus* can be compared to plants of *Helleborus* x *ballardiae* X *Helleborus* x *hybridus* 'COSEH 6500', disclosed in a U.S. Plant Patent application filed concurrently. Plants of the new *Helleborus* differ primarily from plants of 'COSEH 6500' in plant and growth habit as plants of the new *Helleborus* are taller and more vigorous than plants of 'COSEH 6500'.

Plants of the new *Helleborus* can be compared to plants of *Helleborus* x *ballardiae* X *Helleborus* x *hybridus* 'COSEH 6600', disclosed in a U.S. Plant Patent application filed concurrently. Plants of the new *Helleborus* differ primarily from plants of 'COSEH 6600' in flower color as plants of the new *Helleborus* have light yellow green-colored flowers with greyed purple-colored margins whereas plants of 'COSEH 6600' have greyed purple to greyed red-colored flowers. In addition, plants of the new *Helleborus* are taller and more vigorous than plants of 'COSEH 6600'.

Plants of the new *Helleborus* can also be compared to plants of *Helleborus* x *hybridus* 'ABCRD01' (U.S. Plant Pat. No. 24,149) also known as trade name 'Penny's Pink'. In side-by-side comparisons, plants of the new *Helleborus* differ primarily from plants of 'Penny's Pink' in the following characteristics:

1. Plants of the new *Helleborus* have dark green-colored leaves without distinct venation whereas plants of 'Penny's Pink' have green-colored leaves with distinct venation.
2. Plants of the new *Helleborus* differ from plants of 'Penny's Pink' in flower color as plants of the new *Helleborus* have light yellow green-colored flowers with greyed purple-colored margins whereas plants of 'Penny's Pink' have greyed purple-colored flowers.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1 of 2) is a side perspective view of a typical flowering plant of 'COSEH 6400' grown in a container.

Figure 2:
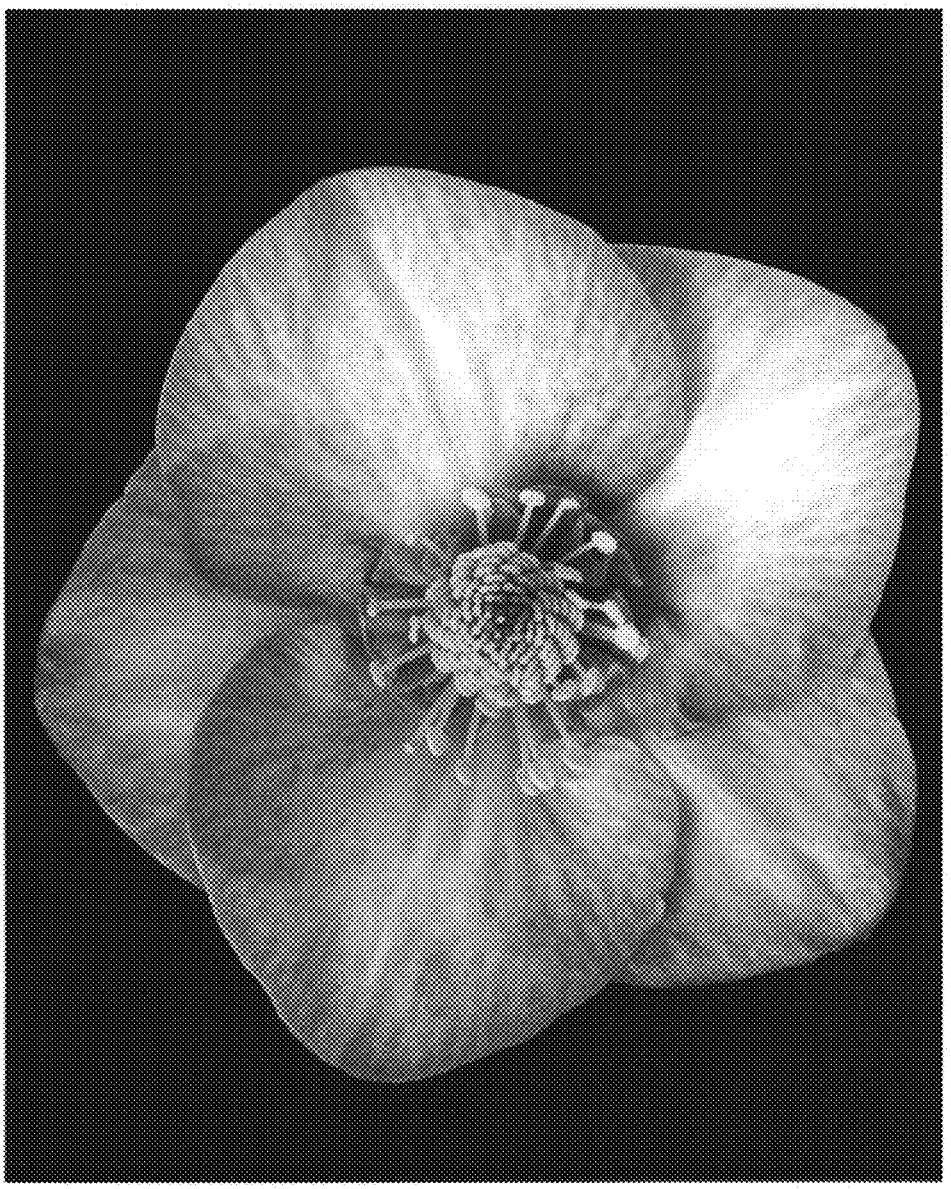

The photograph on the second sheet (FIG. 2 of 2) is a close-up view of a typical flower of 'COSEH 6400'.

DETAILED BOTANICAL DESCRIPTION

The aforementioned photographs and following observations, measurements and values describe plants grown during March in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were four months old when the photographs and the description were taken. In the following description, color references are made to The Royal Horticultural Society Colour Chart, 2015 Edition, except where general terms of ordinary dictionary significance are used.

Botanical classification: *Helleborus* x *ballardiae* X *Helleborus* x *hybridus* 'COSEH 6400'.

Parentage:

*Female, or seed, parent*.—Proprietary selection of *Helleborus* x *ballardiae* disclosed as code number P839, not patented.

*Male, or pollen, parent*.—Unnamed selection of *Helleborus* x *hybridus*, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from 4° C. to 15° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to slightly outwardly spreading and mounding plant habit with flowers held within and above the foliar plane; plant shape, roughly flattened globular; vigorous growth habit and rapid growth rate.

*Plant height, soil level to top of foliar plane*.—About 34.5 cm.

*Plant height, soil level to top of flowers*.—About 59.2 cm.

*Plant diameter* (*area of spread*).—About 67 cm.

Leaf description:

*Arrangement*.—Leaves arranged in a basal rosette; leaves palmately compound with typically five leaflets per leaf.

*Leaf length*.—About 21.3 cm.

*Leaf width*.—About 24.4 cm.

*Leaflet length*.—About 14.3 cm.

*Leaflet width*.—About 7.8 cm.

*Leaf shape*.—Palmate; reniform in outline.

*Leaflet shape*.—Elliptic to ovate.

*Leaflet apex*.—Bluntly acute.

*Leaflet base*.—Attenuate.

*Leaflet margin*.—Serrate; coarsely undulate.

*Leaflet texture and luster, upper surface*.—Smooth, glabrous; leathery; glossy.

*Leaflet texture and luster, lower surface*.—Smooth, glabrous; leathery; slightly glossy.

*Leaflet venation pattern*.—Pinnate.

*Leaflet color*.—Developing leaflets, upper surface: Close to NN137A; midvein, close to 145B and proximally tinged with close to 177A and 177B. Developing leaflets, lower surface: Close to 147B; midvein, close to 177A. Fully developed leaflets, upper surface: Darker than between 139A and 147A; venation, close to 145A and at the base, close to N186C. Fully developed leaflets, lower surface: Close to 147B; venation, close to 148D tinged with close to 177B.

*Petioles*.—Length: About 18.2 cm. Diameter: About 7 mm to 8 mm. Strength: Strong. Texture and luster, upper and lower surfaces: Smooth, glabrous; slightly glossy. Color, upper and lower surfaces: Close to 143C moderately to heavily covered with fine dots, close to 187A and proximally, close to N186C.

Flower description:

*Flower shape and habit*.—Rotate flowers; flowers slightly cupped; arranged in panicles; freely flowering habit with about seven flowers per inflorescence and about 77 flowers developing per plant; flowers face mostly outwardly to slightly nodding and slightly upright.

*Fragrance*.—None detected.

*Natural flowering season*.—Plants begin flowering about ten months after planting; plants flower naturally from winter into the late winter in Germany.

*Flower longevity on the plant*.—About ten days; sepals persistent, other flower parts are not persistent.

*Flower buds*.—Length: About 1.5 cm. Diameter: About 1.1 cm. Shape: Broadly ovate to oblong. Texture and luster: Smooth, glabrous; matte. Color: Close to 145B; towards the base, close to 145C; venation, close to 186C.

*Inflorescence height* (*including peduncle*).—About 55.4 cm.

*Inflorescence diameter*.—About 22.7 cm.

*Flower diameter*.—About 6.9 cm by 6.9 cm.

*Flower depth* (*height*).—About 2.4 cm.

*Petals*.—All petals are transformed into nectaries.

*Sepals*.—Quantity and arrangement: About five, arranged in a single whorl. Length: About 3.6 cm. Width: About 3.2 cm. Shape: Broadly ovate to broadly rhomboidal, slightly concave. Apex: Obtuse. Base: Truncate to broadly cuneate. Margin: Entire; not undulate to slightly undulate. Texture and luster, upper surface: Smooth, glabrous; matte. Texture and luster, lower surface: Smooth, glabrous; slightly glossy. Color: When opening, upper surface: Close to 145C; towards the margins and apex, close to 145D; venation, similar to lamina. When opening, lower surface: Close to 145C; center, tinged and flushed with close to 186B to 186C; venation, similar to lamina. Fully opened, upper surface: Close to 145B; towards the margins and apex, tinged with close to 186A; venation, similar to lamina; with development, color becoming closer to 147C and towards the margins and apex, moderately to strongly tinged with close to 183D. Fully opened, lower surface: Close to 145B to 145C; towards the margins and apex, moderately to strongly tinged with close to 186A; venation, similar to lamina; with development, color becoming closer to 147B strongly tinged with close to 183B.

*Flower bracts*.—Quantity per flower: Typically one or two. Length: About 4.6 cm. Width: About 2.8 cm. Shape: Ovate. Apex: Acute, occasionally cleft to tri-lobed. Base: Truncate. Margin: Sparsely and finely serrate; slightly undulate. Color, upper surface: Close to between 137B and 143A; venation, similar to lamina. Color, lower surface: Close to between 138B and 147B; venation, close to 177A.

*Peduncles*.—Length: About 48.5 cm. Diameter: About 1 cm. Aspect: About 10° from vertical. Strength: Strong. Texture and luster: Smooth, glabrous; moderately glossy. Color: Close to 145A, heavily covered with fine dots, close to 183A.

*Pedicels*.—Length: About 1.9 cm. Diameter: About 2.5 mm. Aspect: About 10° to 22.5° from peduncle axis. Strength: Moderately strong. Texture and luster: Smooth, glabrous; moderately glossy. Color: Close to 145B, sparsely covered with fine dots, close to 182A.

*Reproductive organs*.—Stamens: Quantity per flower: About 60. Filament length: About 1.2 cm. Filament color: Close to 157D. Anther shape: Double and broadly reniform; basifixed. Anther size: About 2 mm by 1.75 mm. Anther color: Close to 150D. Pollen amount: Moderate. Pollen color: Close to 4D to lighter than 4D. Pistils: Quantity per flower: About four to seven. Pistil length: About 1 cm. Stigma diameter: About 0.3 mm. Stigma shape: Club-shaped. Stigma color: Close to 157D. Style length: About 9 mm. Style color: Close to 186C. Ovary color: Close to 150D. Nectaries (transformed petals): Quantity per flower: About 13. Length: About 1.4 cm. Diameter: About 5 mm. Shape: Tubular, flattened. Texture and luster, inner and outer surfaces: Smooth, glabrous; slightly glossy. Color, immature, inner surface: Close to 145C; towards the base, close to 145A. Color, immature, outer surface: Close to 145C; towards the base, close to 145A; basal spot, close to 151B. Color, mature, inner surface: Close to 150B to 150C; towards the base, close to N144B; with development, becoming closer to 151A to 151B. Color, mature, outer surface: Close to 150B to 150C; towards the base, close to N144B; basal spot, close to 152C; with development, becoming closer to 151A to 151B and basal spot, close to 153D.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 6400' as illustrated and described.

* * * * *